(12) United States Patent
Trudeau et al.

(10) Patent No.: US 6,378,289 B1
(45) Date of Patent: Apr. 30, 2002

(54) METHODS AND APPARATUS FOR CLAMPING SURGICAL WIRES OR CABLES

(75) Inventors: Jeffrey L. Trudeau, MQT; Thomas S. Kilpela, Marquette, both of MI (US)

(73) Assignee: Pioneer Surgical Technology, Marquette, MI (US)

( * ) Notice: Subject to any disclaimer, the term of this patent is extended or adjusted under 35 U.S.C. 154(b) by 0 days.

(21) Appl. No.: 09/442,293

(22) Filed: Nov. 19, 1999

(51) Int. Cl.[7] ............................................. A61B 17/56
(52) U.S. Cl. ......................... 60/103; 606/74; 24/134 R
(58) Field of Search ..................... 24/134 KB, 134 R; 606/103, 74, 83

(56) References Cited

U.S. PATENT DOCUMENTS

| | | | |
|---|---|---|---|
| 4,881,303 A | * 11/1989 | Martini | 24/170 |
| 4,912,817 A | * 4/1990 | Sandried | 24/132 R |
| 4,966,600 A | * 10/1990 | Songer et al. | 606/74 |
| 5,083,350 A | * 1/1992 | Sandried | 24/134 R |
| 5,312,410 A | * 5/1994 | Miller et al. | 606/86 |
| 5,395,374 A | * 3/1995 | Miller et al. | 606/74 |
| 5,395,375 A | 3/1995 | Turkel et al. | 606/83 |
| 5,449,361 A | * 9/1995 | Preissman | 606/103 |
| 5,531,297 A | * 7/1996 | Pipan | 188/65.1 |
| 5,569,253 A | * 10/1996 | Farris et al. | 606/74 |
| 5,788,351 A | * 8/1998 | Prunty et al. | 312/326 |
| 5,788,697 A | * 8/1998 | Kipela et al. | 606/74 |
| 5,902,305 A | * 5/1999 | Beger et al. | 606/103 |
| 5,935,130 A | * 8/1999 | Kipela et al. | 606/74 |

* cited by examiner

*Primary Examiner*—Gene Mancene
*Assistant Examiner*—Michael B. Priddy
(74) *Attorney, Agent, or Firm*—Banner & Witcoff, Ltd.

(57) ABSTRACT

A device for clamping cables or wires or other elongate members used in surgical fastening procedures includes a generally cylindrical housing having a bore for receiving a cable. A saddle member is movably mounted with respect to the housing and includes a saddle jaw that may selectively be moved into engagement with a cable disposed in the bore. A cam lever having a cam surface engages a cam support surface on the housing for actuating the saddle member and thereby selectively clamping the cable. The saddle jaw cooperates with a housing jaw on the housing for redirecting the cable into an undulating path when the cam lever is moved to a clamping position. The cam lever is provided with multiple facets dimensioned to provide optimum clamping force to different sized cables. The facets also provide a positive tactile indication to a user that the cam lever is in one of multiple clamping positions. The clamp advantageously applies a clamping force to the cable through the saddle and without direct contact between the cam lever and the cable, thereby reducing abrasion and shear forces applied to the cable as compared to prior art devices. The clamp is also provided with releasable couplings for selective attachment to a cable guide assembly and a tensioning tool.

12 Claims, 5 Drawing Sheets

METHODS AND APPARATUS FOR CLAMPING SURGICAL WIRES OR CABLES

BACKGROUND OF THE INVENTION

1. Field of the Invention

The invention relates generally to surgical methods and apparatus for clamping cables or wires. More particularly, the invention relates to methods and apparatus for clamping cables, wires or other elongate members used in orthopedic surgical techniques.

2. Description of the Prior Art

Surgical cables and wires are now used extensively in orthopedic surgery for securing bones and bone fragments in place and for fastening surgical implements to bones. Typically, surgical cables are implanted using tensioning devices, which apply tension to a cable looped around the bone, and crimps that are deformed to clamp the cable loop in place.

The prior art is typified by U.S. Pat. No. 5,395,375 to Miller et al, the entire writing of which is incorporated herein by reference. The disclosed technique involves the use of a small lever-action cable clamp located along the cable between the crimp and the tensioning tool. A first cable may be provided with a pre-final amount of tension and then the cable clamp operated to secure the first cable in the pre-final position. The tensioning tool may then be removed from the first cable and used in conjunction with another cable clamp, to apply tension to a second cable. This technique permits the readjustment of the tension on the cables used in an orthopedic application.

Cable clamps like of the prior art incorporate a cam lever that bears directly on the cable surface. Thus, as the cam lever is operated to clamp the cable, the clamping force is applied to a relatively small area of the cable surface and the cable is subjected to potentially damaging shear and compressive forces. This may result in local weakening of the cable, which is undesirable especially since the cable may be in place for long periods of time and subject to repetitive stresses and any weakened portion will represent the potential for failure of the cable. It would therefore be desirable to provide an improved cable clamp that can be used to temporarily clamp a cable without subjecting the cable to potentially damaging localized stresses.

Another problem with cable clamps of the prior art is that they do not provide for efficient and risk-free operation with a variety of different sized cables. Different sized cables are employed in surgical operations, depending on the particular application. Cable clamps like the one disclosed by Miller and described above, are configured to have only an open and closed position, with the closed position applying the maximum clamping force to the cable. When used with larger cable diameters, prior art devices may apply excessive and damaging forces to the cable when the cam is moved to the clamping position. It would therefore be desirable to provide a cable clamping device having a single design that may be used to efficiently and safely clamp cables having different diameters or lateral dimension.

Yet another shortcoming of prior art cable clamps is that they do not provide stable locking positions or positive indication to a surgeon as to when suitable clamping force has been applied to the clamped cable. For example, prior art devices like the one described by Miller use a cam lever having a smooth cam surface without predefined locking positions. Thus, a physician must rely only on the tactile sensation of continuously increasing forces applied to the cam lever to determine when sufficient clamping force is applied to the cable. It would therefore be desirable to provide a cable clamp which has at least one pre-defined locking position and which provides a positive tactile indication to a surgeon that sufficient yet safe clamping force has been applied to the clamped cable. It would further be desirable to provide such stable locking positions and positive tactile indication for more than one size of cable to be used with the cable clamp.

SUMMARY OF THE INVENTION

The aforementioned problems are addressed by the present invention, which in a preferred embodiment, provides a clamping device that incorporates a cable housing having a cable bore defined therein and cam operated saddle member adapted to move with respect to the housing. The saddle member is actuated by a cam lever which is provided with a cam surface that engages the cable housing. In a preferred embodiment, the cam lever is movably secured to the saddle member by a pivot pin. Movement of the cam lever results in movement of the saddle member in a direction that is generally transverse to the cable bore. Since the cam surface does not act directly on the cable surface and since the saddle member applies force in a direction that is generally transverse to the cable, the cable may be clamped in a safe and efficient manner without potentially damaging compressive or shear forces being applied.

According to another aspect of the invention, the clamping device is provided with at least one locking jaw that is adapted to redirect the cable and enhance the clamping capability. In a preferred embodiment, the locking jaw is provided with an undulating surface and is fastened to the saddle member so as to redirect the cable from a substantially straight path to a non-straight, for example, undulating or serpentine path when the saddle member is moved to a clamping position. In another embodiment, both the saddle member and the housing are provided with cooperating jaws that define a non-straight, for example, undulating or serpentine path, when the saddle member is in a clamping position. Since the cable is redirected to a non-straight path, the clamping forces is distributed to a greater surface area of the cable, thereby reducing the potential for damaging localized stress concentrations and reducing the normal force necessary to safely clamp the cable.

According to yet another aspect of the invention, the clamping device is provided with a cam having a plurality of locking positions that enable a surgeon to determine by a positive tactile indication that sufficient clamping force has been applied to the cable. In a preferred embodiment, the locking positions are defined by facets on the cam surface, which may be flattened portions. The dimensions of the facets are selected based on the lateral dimensions of different-sized cables or wires that are to be used with the clamping device. Thus, as the cam lever is rotated to a pre-defined locking position, the surgeon is given a tactile indication as to when the cam lever is in one of its pre-defined locking positions.

DETAILED DESCRIPTION OF THE PREFERRED EMBODIMENT

Figure 1:
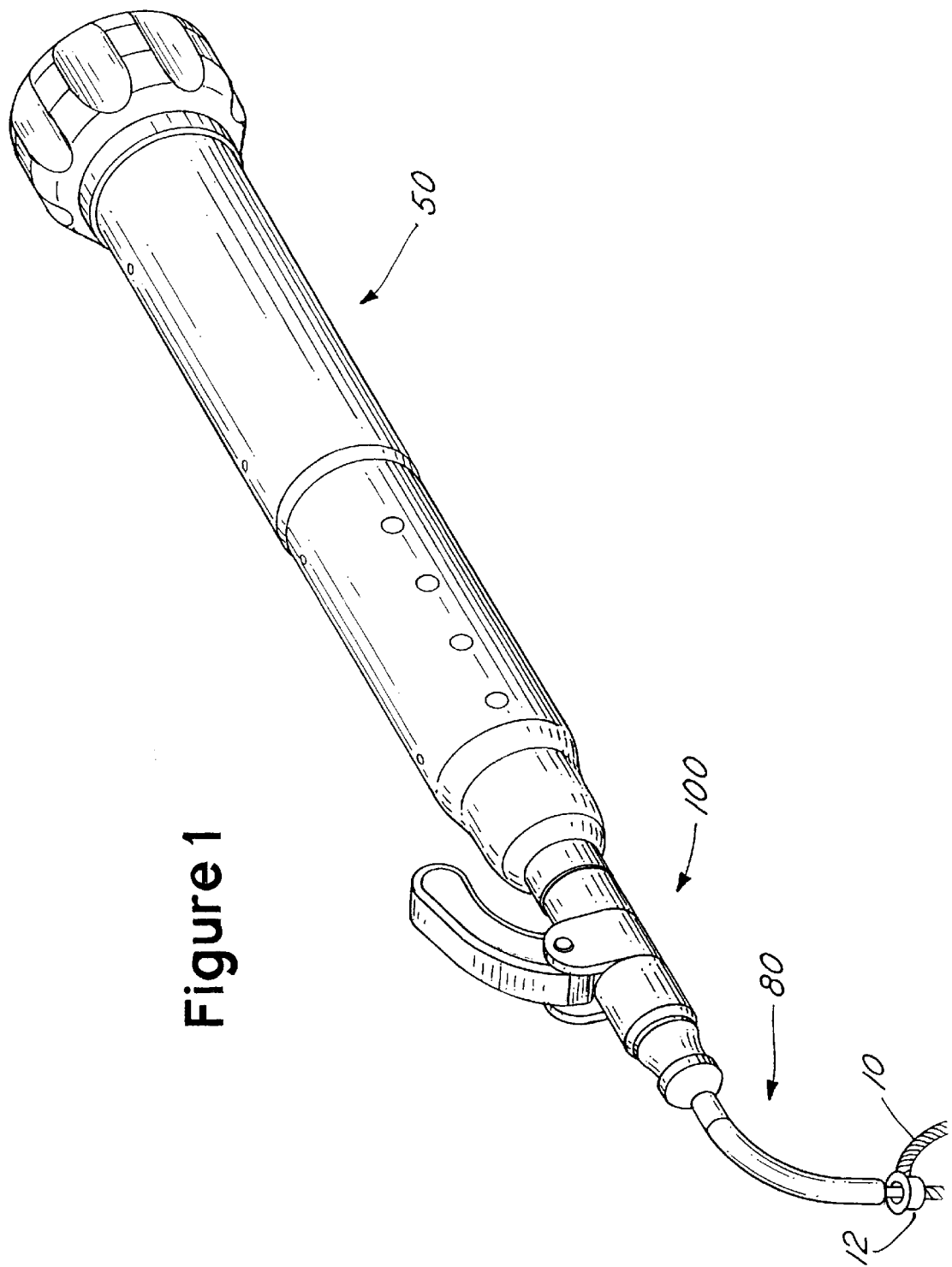
FIG. 1 is an plan view of an exemplary cable clamp according to the invention in use with a cable tensioning tool.

FIG. 1 illustrates an exemplary cable clamp 100 according to a preferred embodiment of the invention illustrated as part of a larger assembly that includes a tensioning tool 50 and a cable guide assembly 80. Although the invention will be described with reference to an exemplary cable clamp, it is not intended to be limited to devices for clamping cables, but is intended to encompass devices for clamping wires and other elongate members. Tensioning tool 50 provides a mechanism for applying a measured tension to cable 10, which extends through a "top hat" crimp 12 to form a loop for orthopedic fastening. As is known in the art, one end of the cable 10 is secured around the outside of the crimp and the other end extends through a bore in the crimp, through cable guide assembly 80, through a bore in cable clamp 100 and into the tensioning tool where it is gripped by a mechanism, the details of which are not important for an understanding of the invention.

Cable guide assembly 80 functions to prevent abrupt bending in the cable during application of the tensioning force to the cable 10. As will be apparent to those of ordinary skill, cable 10 will typically be one of a number of cables used as loop fasteners in a particular surgical application. Clamp 100, the details of which will be explained below, provides a means for temporarily clamping the cable 10 after a measured tension has been applied thereto. After initially tensioning cable 10, a surgeon will typically remove the tensioning tool 50 from engagement with the clamping device and cable 10, and use the tensioning tool to apply tension to another cable fastener (not shown) used in the surgical application in conjunction with another clamp (not shown) for temporarily clamping the tensioned cable. After tensioning the other cable, the tension of cable 10 may be readjusted by engaging the cable with the tensioning tool and re-tensioning the cable 10. In this manner, the tensions of all cables used in the procedure may be optimized before the cables are semi-permanently affixed by deforming the crimp elements 12.

Figure 2:
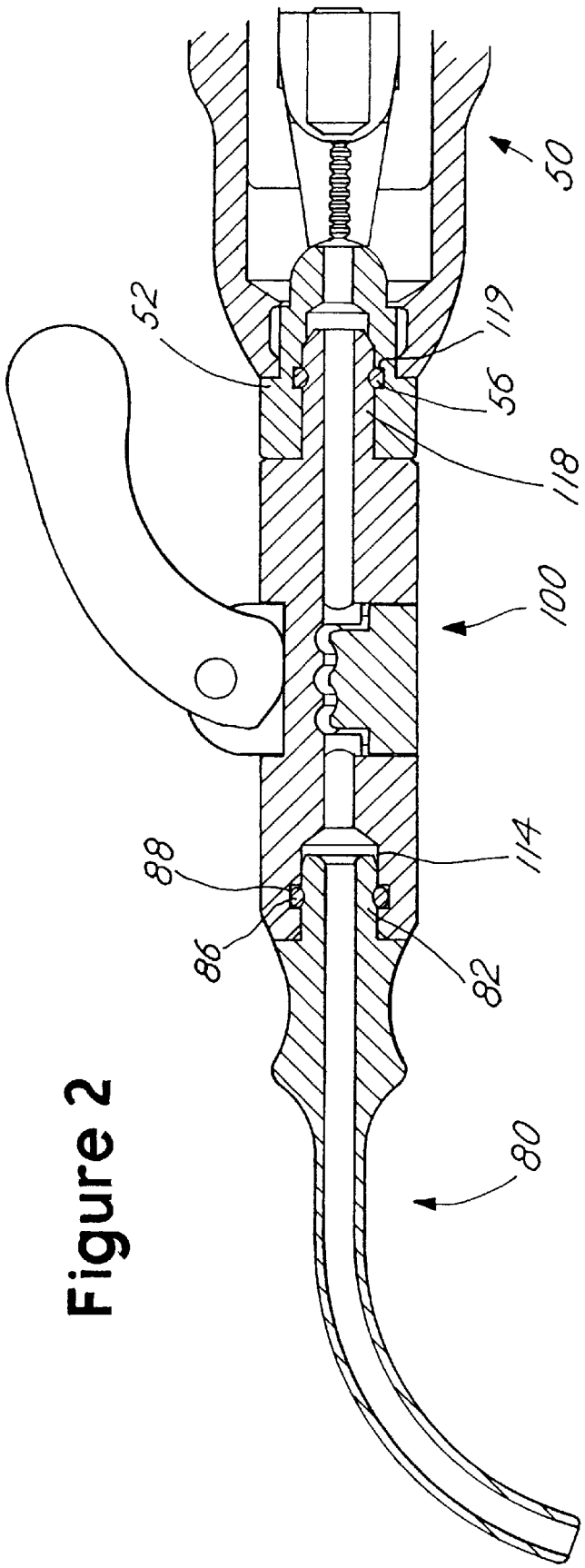
FIG. 2 is a cutaway of a cable clamp and cable tensioning tool illustrated in FIG. 1.

Referring additionally to FIG. 2, which is a partial section of the cable clamp 100, guide assembly 80 and tensioning tool 50, cable clamp 100 is secured to both tensioning tool 50 and cable guide assembly 80 using releasable connecting elements. The cable 10 (FIG. 1) has been omitted from this illustration for clarity. Guide assembly 80 includes a generally cylindrical guide barrel 82 which is received in a complementarily-shaped clamp socket 114. A deformable ring 86 is disposed in a guide barrel recess 84 and cooperates with an annular recess formed on the outer surface of guide barrel 82. Deformable ring 86 may be preferably formed of a coil spring element. As will be apparent to those of ordinary skill, deformable ring 86, in conjunction with guide barrel recess 84 and the annular recess on guide barrel 82, provides a releasable coupling that enables removal of guide 80 from clamp 100 with the application of a generally longitudinal force. A similar coupling is provided on an opposite end of cable clamp 100. Tensioning tool is provided with a tensioning tool socket 52, including an annular recess formed therein and retaining a deformable ring 56. Cable clamp 100 is provided with a clamp barrel 118 including an annular recess 119 which is releasably received in tensioning tool socket 52. Thus, guide 80, clamp 100 and tensioning tool 50 may be releasably assembled together.

Figure 3A:
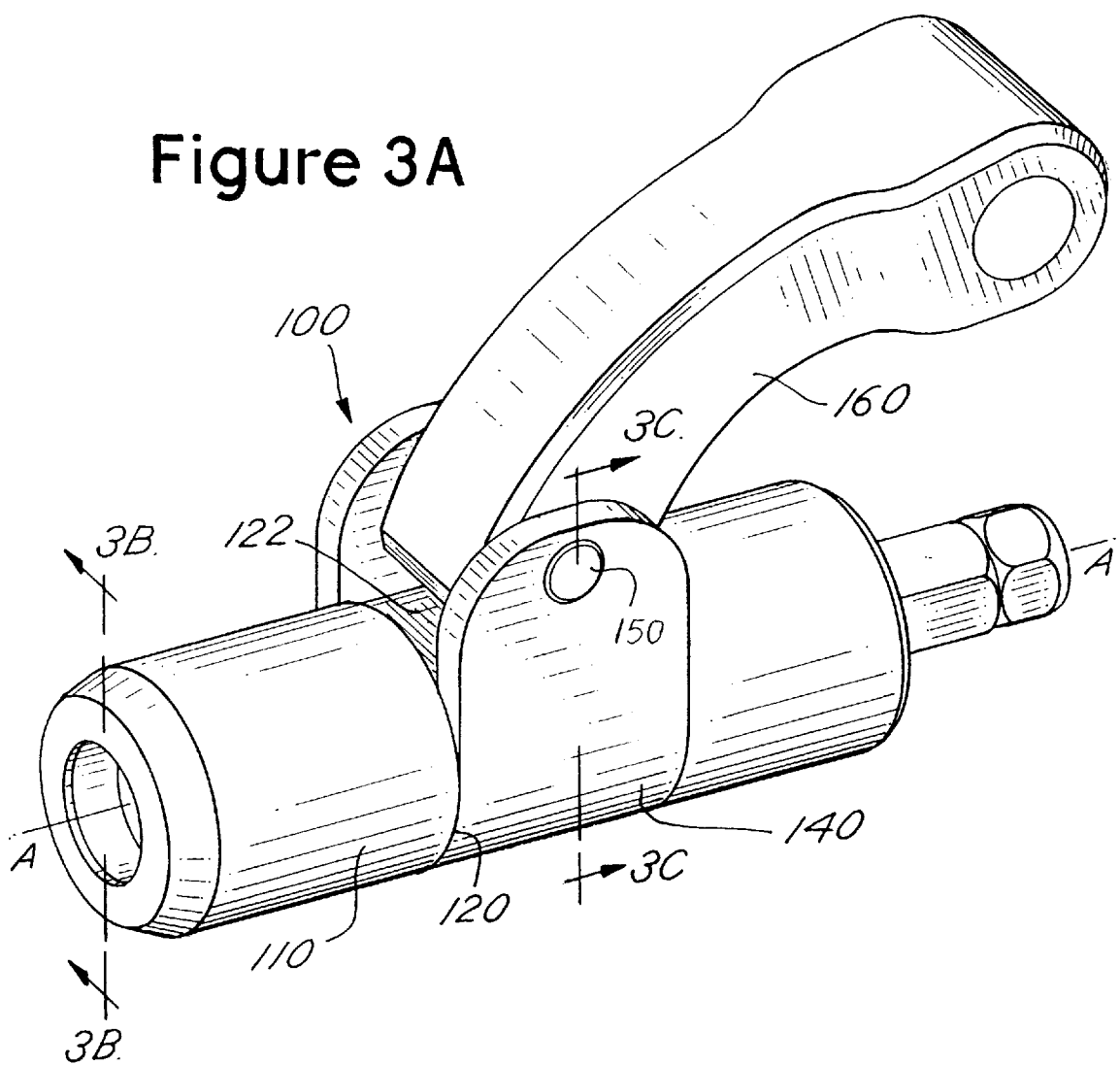
FIG. 3A is an isometric of an exemplary cable clamp according to the invention.
Figure 3C:
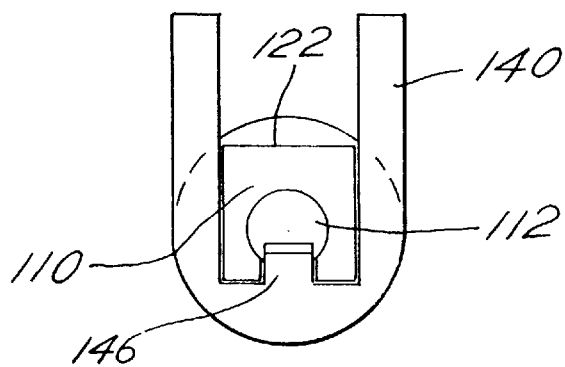
FIG. 3C is a section view taken along lines 3C—3C of FIG. 3A.
Figure 3B:
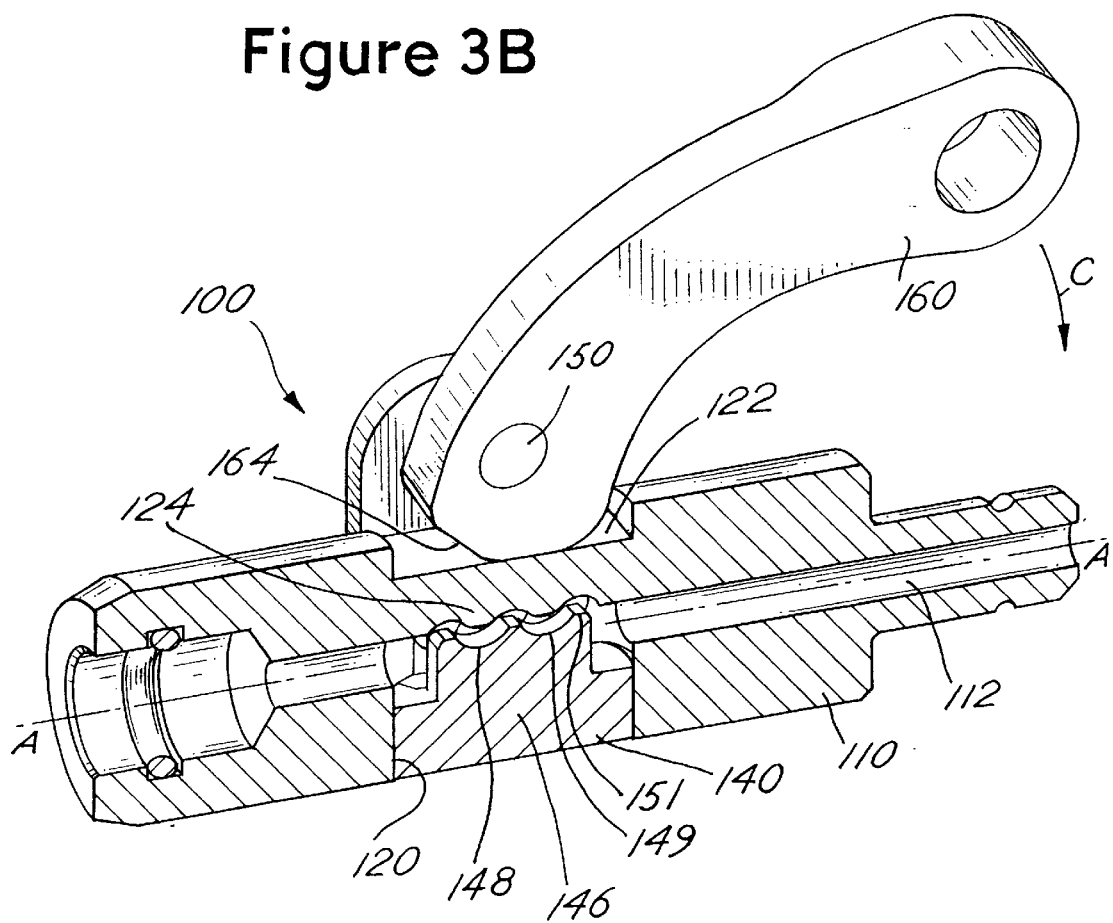
FIG. 3B is a section taken along a plane defined by line 3B—3B in FIG. 3A.

FIGS. 3A and 3B illustrate a cable clamp 100 according to a preferred embodiment of the invention. An exemplary cable clamp 100 is comprised of a generally cylindrical housing 110, which is provided with generally U-shaped saddle 140 movably mounted thereon. Saddle 140 is disposed within a saddle guide 120 formed in the housing 110. A cam lever 160 pivotably cooperates with saddle 140 by way of a pivot pin 150 retained within holes formed in the legs of the saddle 140. Cam lever 160 includes a cam surface 164 which engages a cam support surface 122 provided on the housing 110. As cam lever 160 is pivoted with respect to saddle 140 in a clamping direction, indicated by arrow C, saddle 140 is moved in a direction generally transverse to the longitudinal axis (A—A) of housing 110 to apply a clamping force to the cable (not shown) as will be described below.

Referring specifically to FIG. 3B, saddle 140 is provided with a generally rectangular-shaped saddle jaw 146 that defines an undulating saddle jaw surface 148. As illustrated and in order to simplify manufacture, saddle jaw surface 146 is formed from a series of curved recesses 149 separated by flat portions 151. The invention contemplates other jaw surface shapes, however, including serpentine jaw surfaces which include smooth transitions compared to the illustrated curved recesses 149 and flat portions 151. As will be recognized by those of ordinary skill, saddle jaw 146 does not necessarily have to be formed homogenously with saddle 140, but may be machined as a separate part and fastened to saddle 140 using conventional fastening techniques, such as welding or threaded fasteners. Saddle jaw 146 extends into the bore 112 of housing 110 for engaging a periphery of the cable (not shown in FIG. 3B). Saddle jaw 146 cooperates with a complementarily-shaped housing jaw 124 in order to form a generally undulating clamping space. The undulating surface of housing jaw 124 shown in FIG. 3B may be formed as a series of annular ribs within the housing bore 112.

Referring additionally to FIG. 3C, saddle jaw 146 is disposed within a generally rectangular saddle jaw guide 150 formed in the housing 110 on a side opposite cam support surface 122. Saddle jaw 146 can therefore move within the saddle jaw guide 150 in a direction generally perpendicular to the housing bore axis.

As will be appreciated by those of ordinary skill, the movement of the cam lever 160 from a released position in the direction of arrow C (FIG. 3B) to a clamping position causes the cam surface 164 to move with respect to the cam support surface 122, thereby moving saddle 140 within saddle guide 120 in a direction substantially transverse to the longitudinal extent of bore 112 and into a clamping position. The housing jaw surface 126 and the saddle jaw surface 148 cooperate to redirect the cable from a substantially straight path to an undulating path when the saddle 140 is moved to a clamping position. It will be appreciated that the undulating surfaces of the saddle jaw and housing jaw increase the area of the cable to which the clamping force is applied. Thus, the amount of force that may be safely applied to a cable without risk of damage is increased compared to prior art clamping devices.

Figure 4:
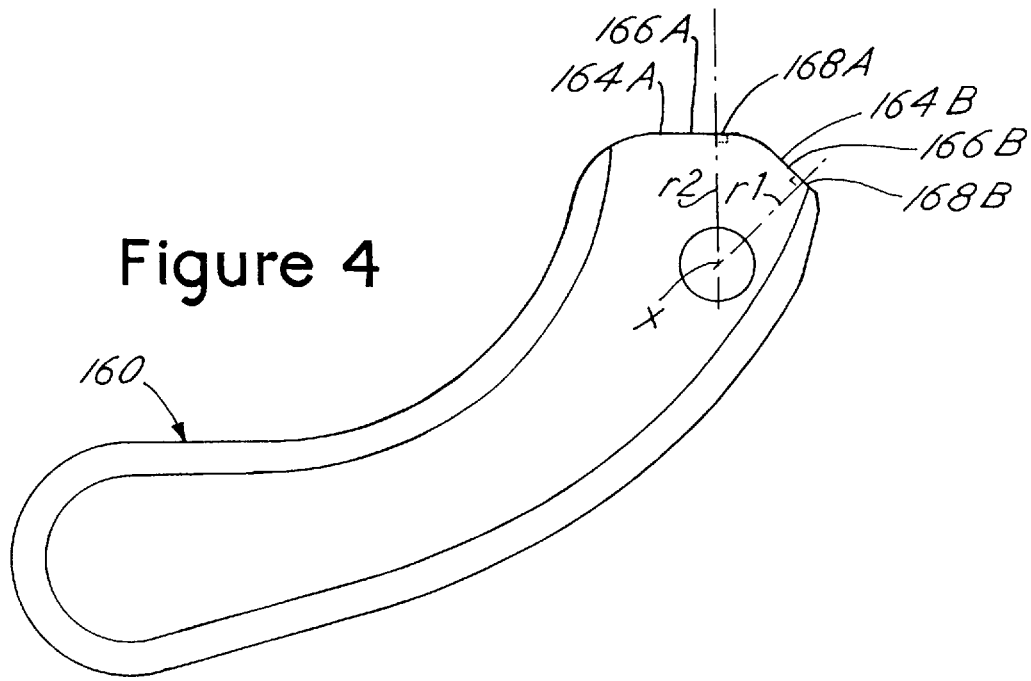
FIG. 4 is a side view of a cam lever according to a preferred embodiment of the present invention.

According to another aspect of the invention, cam lever 160 is provided with a multi-faceted cam surface. Referring to FIG. 4, an exemplary cam surface 164 includes two facets: facet 164A and facet 164B, which each define a clamping position for clamping cables of two respective sizes, as will be explained below. Each facet 164A and 164B of the cam lever 160 is preferably provided as a substantially flat surface for engaging the cam support surface 122 on the housing 110. Each facet has associated with it a radial dimension r1 and r2 measured from the cam lever pivot axis (X). The radial dimensions are selected to provide optimum clamping force for corresponding cable sizes that are expected to be used with the cable clamp. Preferably, cam surfaces 164A and 164B are provided with respective flat portions that extend on both sides of respective radial lines r1 and r2 in order to facilitate the positive locking aspects of the invention. That is, cam surface 164A includes a first flat portion 166A to the left of the point where radial line r2 intersects the cam surface 164A. Cam surface 164A also includes a second, smaller flat portion 168A that extends, for example for 0.025 inches, to the left of the point were radial line r2 intersects cam surface 164A. Cam surface 164B is provided with similar flat surface portions 166B and 168B. The two flat surface portions extending on both sides of the radial lines r1 and r2 (the radial lines also being perpendicular to the respective cam surfaces 164B and 164A) provide for stable locking positions of the cam lever 160 and positive tactile indication that the locking positions have been reached.

Figure 5A:
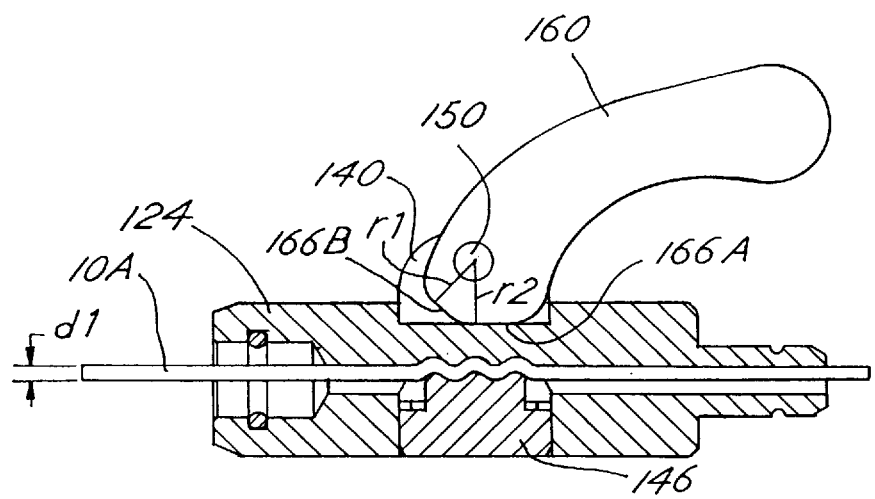
FIGS. 5A and 5B show cross-sections of an exemplary cable clamp according to the invention in two respective clamping positions for two different sized cables.
Figure 5B:
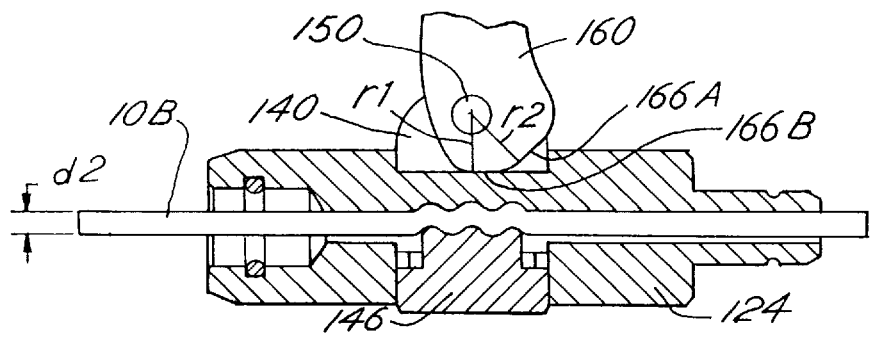

FIGS. 5A and 5B illustrate a clamp according to a preferred embodiment of the present invention being used with two different sized cables. As shown in FIG. 5A, a first cable 10A having a lateral dimension d1 is clamped between housing jaw 124 and saddle jaw 146 and cam lever 160 is positioned at a first clamping position. In the first clamping position, saddle jaw 146 and housing jaw 124 are disposed a predetermined and optimum distance from one another to provide a maximum safe clamping force to the first-sized cable 10A. Referring now to FIG. 5B, in accordance with the invention, the cable clamp 100 can be used to efficiently and safely clamp a second cable 10B of a second lateral dimension d2. As will be apparent, by virtue of the first radial dimension r1 of the cam lever 160, saddle jaw 146 is disposed further from housing jaw 124 than in the clamping position illustrated in FIG. 5A. Saddle jaw 146 is disposed an optimum distance from housing jaw 124 to provide the maximum safe clamping force to cable 10B.

As will be recognized by those of ordinary skill, the clamp of the invention advantageously applies a clamping force to the cable without direct contact between the cam lever and the cable, thereby preventing damage from abrasion and shear forces. Clamping force is applied through the saddle, which applies a lateral force against the cable surface and redirects the cable into an undulating path defined between the housing jaw and saddle jaw. Thus, the potential for damage to the cable surface is reduced compared to prior art cable clamps. Moreover, less clamping force is required since a greater surface area of the cable 10 is engaged by clamping jaw surfaces as compared to flat clamping jaw surfaces.

It will also be recognized that clamping devices in accordance with the invention may be used to clamp different sized cables, without refitting parts or clamping jaws with new dimensions. Moreover, the clamping devices according to the invention provide for positive tactile determination as to when the cam lever 160 has been moved to one of a plurality of clamping positions.

Although the preferred embodiment of this invention has been described hereinabove in some detail, it should be appreciated that a variety of embodiments will be readily available to persons utilizing the invention for a specific end use. The description of this invention is not intended to be limiting on this invention, but is merely illustrative of the preferred embodiment of this invention. Other products, apparatus and methods which incorporate modifications or changes to that which has been described herein are equally included within this application. Additional objects, features and advantages of the present invention will become apparent by referring to the above description of the invention in connection with the accompanying drawings.

What is claimed is:

1. A clamp for clamping elongate members of varying lateral dimension, the clamp comprising:
   a housing for receiving the elongate member, the housing having a bore extending therethrough;
   a saddle member movably mounted with respect to the housing;
   a cam lever cooperating with the saddle member and having a cam surface for moving the saddle member relative to the housing; and
   an engaging surface associated with the saddle member for engaging a periphery of the elongate member.

2. The clamp of claim 1 wherein the cam surface formed on the cam lever has at least two facets.

3. The cable clamp of claim 1, wherein the engaging surface is formed as an undulating surface.

4. The clamp of claim 1, wherein the cam lever is pivotably attached to the saddle member.

5. The clamp of claim 1, wherein the cam lever includes an arm for permitting a user to actuate the saddle member.

6. The clamp of claim 1, wherein the cam surface is adapted to engage a surface on the housing.

7. The clamp of claim 1, wherein the engaging surface is shaped to redirect the elongate member from a substantially straight path.

8. The clamp of claim 1, wherein the engaging surface is shaped to redirect the elongate member into a serpentine path.

9. The clamp of claim 1, wherein the engaging surface is formed on a saddle jaw extending from the saddle.

10. The clamp of claim 9, further comprising a housing jaw formed in the housing and cooperating with the saddle jaw.

11. A method of using the clamp of claim 1, the method comprising the steps of:
    looping the elongate member around a bone;
    inserting an end of the elongate member through the housing bore;
    applying tension to the elongate member; and
    operating the cam lever to apply a clamping force to the elongate member and in so doing, redirecting the elongate member to an undulating path.

12. A method of clamping an elongate orthopedic member, such as a cable or wire, the method comprising the steps of:
    looping the elongate member around a bone;
    inserting an end of the elongate member into a clamping device;
    applying a clamping force to the elongate member using the clamping device and in so doing, redirecting the elongate member to an undulating path.

* * * * *